United States Patent
Meskens

(10) Patent No.: US 11,904,167 B2
(45) Date of Patent: Feb. 20, 2024

(54) AUXILIARY DEVICE CONNECTION

(71) Applicant: Cochlear Limited, Macquarie University (AU)

(72) Inventor: Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 284 days.

(21) Appl. No.: 17/413,698

(22) PCT Filed: Mar. 25, 2020

(86) PCT No.: PCT/IB2020/000211
§ 371 (c)(1),
(2) Date: Jun. 14, 2021

(87) PCT Pub. No.: WO2020/194050
PCT Pub. Date: Oct. 1, 2020

(65) Prior Publication Data
US 2022/0016427 A1 Jan. 20, 2022

Related U.S. Application Data

(60) Provisional application No. 62/824,433, filed on Mar. 27, 2019.

(51) Int. Cl.
*A61N 1/36* (2006.01)
*A61N 1/378* (2006.01)
(Continued)

(52) U.S. Cl.
CPC ....... *A61N 1/36038* (2017.08); *A61N 1/3787* (2013.01); *A61N 1/37211* (2013.01);
(Continued)

(58) Field of Classification Search
CPC ............ A61N 1/36038; A61N 1/37211; A61N 1/3787; A61N 1/37252; H04R 25/70;
(Continued)

(56) References Cited

U.S. PATENT DOCUMENTS 5,814,095 A   9/1998   Muller et al.
5,881,158 A   3/1999   Lesinski et al.
(Continued)

FOREIGN PATENT DOCUMENTS

EP   1596629 A3   9/2011
EP   2866886 B1   8/2018
(Continued)

OTHER PUBLICATIONS

Extended Search Report in counterpart European Application No. 20779748.1-1126, dated Oct. 28, 2022, 5 pages.
(Continued)

*Primary Examiner* — Catherine M Voorhees
(74) *Attorney, Agent, or Firm* — Edell, Shapiro & Finnan, LLC

(57) ABSTRACT

An implantable medical system including an implantable stimulator device and an implantable auxiliary device. An implantable cable electrically connects the implantable stimulator device and the implantable auxiliary device. The implantable auxiliary device has an auxiliary device rechargeable battery and an auxiliary component. The implantable medical system is configured to selectively operate in a first mode or a second mode. The implantable medical system is configured to, based on the mode, control charging the auxiliary device rechargeable battery from the implantable stimulator device over the implantable cable and control transmission of an auxiliary device signal from the auxiliary component to the implantable stimulator device over the implantable cable.

20 Claims, 6 Drawing Sheets

(51) Int. Cl.
*A61N 1/372* (2006.01)
*H04R 25/00* (2006.01)

(52) U.S. Cl.
CPC ......... *H04R 25/70* (2013.01); *H04R 2225/31* (2013.01); *H04R 2225/67* (2013.01)

(58) Field of Classification Search
CPC . H04R 2225/31; H04R 2225/67; H02J 7/342; H02J 50/00; H02J 2310/23
See application file for complete search history.

(56) References Cited

U.S. PATENT DOCUMENTS

| | | |
|---|---|---|
| 6,216,040 B1 | 4/2001 | Harrison |
| 6,308,101 B1 | 10/2001 | Faltys et al. |
| 6,636,768 B1 | 10/2003 | Harrison |
| 6,736,771 B2 | 5/2004 | Sokolich et al. |
| 2006/0183965 A1 | 8/2006 | Kasic, II et al. |
| 2010/0274319 A1* | 10/2010 | Meskens ............ A61N 1/36038 607/57 |
| 2010/0317913 A1 | 12/2010 | Conn et al. |
| 2012/0165597 A1 | 6/2012 | Proulx et al. |
| 2012/0265273 A1 | 10/2012 | Libbus et al. |
| 2015/0343225 A1 | 12/2015 | Leigh |
| 2016/0243363 A1 | 8/2016 | Meskens |
| 2017/0113041 A1 | 4/2017 | Karunasiri |
| 2017/0180887 A1* | 6/2017 | Meskens ............... H04B 5/0037 |
| 2018/0050198 A1* | 2/2018 | Mazanec ............ A61N 1/36038 |

FOREIGN PATENT DOCUMENTS

| | | |
|---|---|---|
| WO | 2003030772 A2 | 4/2003 |
| WO | 2018085665 A1 | 5/2018 |
| WO | 2021/038297 A1 | 3/2021 |

OTHER PUBLICATIONS

International Search Report and Written Opinion in counterpart International Application No. PCT/US2020/000211, dated Aug. 7, 2020, 7 pages.

* cited by examiner

AUXILIARY DEVICE CONNECTION

This application is being filed on Mar. 25, 2020, as a PCT International Patent application and claims the benefit of priority to U.S. Provisional patent application Ser. No. 62/824,433, filed Mar. 27, 2019, the entire disclosure of which is incorporated by reference in its entirety.

BACKGROUND

Hearing loss, which can be due to many different causes, is generally of two types: conductive and sensorineural. In many people who are profoundly deaf, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate their auditory nerves in other ways (e.g., electrical, optical, and the like). Cochlear implants are often proposed when the sensorineural hearing loss is due to the absence or destruction of the cochlea hair cells, which transduce acoustic signals into nerve impulses. Auditory brainstem implants might also be proposed when a person experiences sensorineural hearing loss if the auditory nerve, which sends signals from the cochlear to the brain, is severed or not functional.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Technology disclosed herein includes systems, apparatuses, devices, and methods including techniques for interfacing between an implantable primary device and an implantable auxiliary device connected via a cable.

In an example, there is a method including, while an implanted stimulator device is coupled with an external processor device: preventing receiving of an auxiliary device signal over an implanted cable connecting the implanted stimulator device with an implanted auxiliary device; and permitting charging of an auxiliary device battery of the implanted auxiliary device over the implantable cable. In an example, the method further includes, while the implanted stimulator device is not coupled with the external processor device, preventing charging of the auxiliary device battery of the implanted auxiliary device over the implanted cable and permitting receiving of the auxiliary device signal at the implanted stimulator device over the implanted cable.

In examples, the method further includes determining a connection status. The method can further include, responsive to the connection status indicating that the implanted stimulator device is coupled with the external processor device, charging the auxiliary device battery over the implanted cable and ceasing receiving of the auxiliary device signal. The method can further include, responsive to the connection status indicating that the implanted stimulator device is not coupled with the external processor device, ceasing charging of the auxiliary device battery over the implanted cable and receiving the auxiliary device signal at the implanted stimulator device over the implanted cable. In an example, charging the auxiliary device battery over the implanted cable includes: supplying power using two wires of the implanted cable. In an example, receiving the auxiliary device signal at the implanted stimulator device over the implanted cable includes receiving the auxiliary device signal over the two wires. In an example, the method further includes coupling the external processor device to the implanted stimulator device by forming an external device power signal and data signal connection from the external processor device to the implanted stimulator device. In an example, the method further includes, while the implanted stimulator device is coupled with the external processor device, receiving an external processor device data signal from the external processor device at the implanted stimulator device and charging a stimulator device battery of the implanted stimulator device using the external processor device. In an example, the method further includes producing, via an auxiliary component of the implanted auxiliary device, the auxiliary device signal. In an example, the auxiliary component is a data source selected from a group consisting of: a microphone, a transcutaneous wireless audio link, a subcutaneous wireless audio link, a transcutaneous wireless stimulation data link, a subcutaneous wireless stimulation data link, and a telecoil. In an example, the method further includes, while the implanted stimulator device is not coupled with the external processor device and the implanted stimulator device is coupled with a charger device, receiving the auxiliary device signal at the implanted stimulator device over the implanted cable; and charging a stimulator device battery of the implanted stimulator device using the charger device.

In an example, there is an implantable medical system including an implantable stimulator device; an implantable auxiliary device having an auxiliary device battery and an auxiliary component; and an implantable cable configured to electrically connect the implantable stimulator device and the implantable auxiliary device. In an example, the implantable medical system is configured to, based on the implantable medical system being in a first mode or a second mode, control charging the auxiliary device battery from the implantable stimulator device over the implantable cable and control transmission of an auxiliary device signal from the auxiliary component to the implantable stimulator device over the implantable cable.

In an example, the implantable medical system is further configured to, while in the first mode, permit charging of the auxiliary device battery from the implantable stimulator device over the implantable cable and prevent transmitting of the auxiliary device signal from the auxiliary component to the implantable stimulator device over the implantable cable. In an example, while in the second mode, prevent charging of the auxiliary device battery from the implantable stimulator device over the implantable cable and permit transmitting of the auxiliary device signal from the auxiliary component to the implantable stimulator device over the implantable cable. In an example, the implantable stimulator device comprises a switch for selectively permitting and preventing the charging of the auxiliary device battery from the implantable stimulator device based on the implantable medical system being in the first mode or the second mode. In an example, the implantable medical system is configured to operate in the first mode while an external processor device is present and operate in the second mode while the external processor device is absent. In an example, the implantable medical system is configured to operate in the first mode while the implantable stimulator device is coupled with an external processor device and operate in the second mode while the implantable stimulator device is not coupled with the external processor device. In an example, the implantable cable comprises two wires, wherein the two wires are the only wires of the implantable cable electrically connecting the implantable stimulator device and the implantable auxiliary device. In an example, the implantable stimulator device includes a coil for wirelessly coupling with an external processor device, a stimulator device battery, and an electrode assembly configured to deliver stimulation signals to a cochlea of a recipient. In an example, the auxiliary component includes a source selected from a group consisting of: a microphone, a transcutaneous wireless audio link, a subcutaneous wireless audio link, a transcutaneous wireless stimulation data link, a subcutaneous wireless stimulation data link and a telecoil. In an example, the system further includes an external processor device configured to wirelessly provide an external device power signal and data signal to the implantable stimulator device.

In an example, there is an implantable medical apparatus including a wired interface connecting an implantable stimulator device and an implantable auxiliary device. The wired interface prevents the implantable stimulator device from receiving data from the implantable auxiliary device while the implantable stimulator device operates in a first mode. The wired interface prevents the implantable stimulator device from charging the implantable auxiliary device while the implantable stimulator device operates in a second mode. In an example, the implantable stimulator device is configured to operate in the first mode while having an external device data connection. In an example, the implantable stimulator device is configured to operate in the second mode while lacking the external device data connection. In an example, the wired interface comprises two wires, wherein the two wires are the only wires of the wired interface electrically connecting the implantable stimulator device permits receiving of data at the implantable stimulator device from the implantable auxiliary device while the implantable stimulator device operates in the second mode. In an example, the wired interface permits charging of the implantable auxiliary device from the implantable stimulator device while the implantable stimulator device operates in the first mode.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
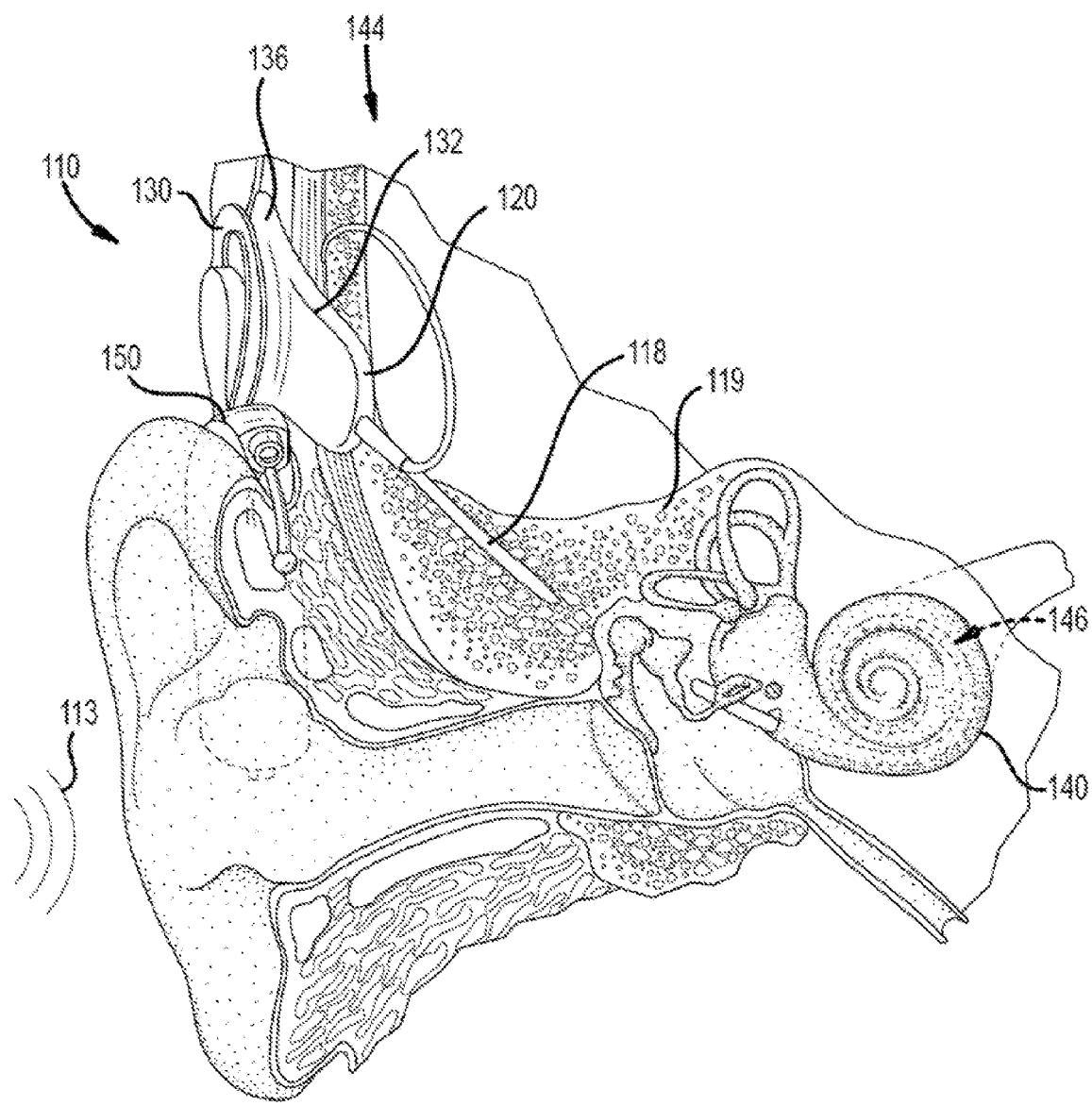
FIG. 1 depicts an example cochlear implant system that can benefit from the technologies disclosed herein.

Disclosed examples include systems having an implantable primary device (e.g., an implantable medical device, such as auditory prostheses) connected to an implantable auxiliary device via a cable. An example system is a totally implantable cochlear implant system having an implantable stimulator device connected to an implantable audio satellite device (e.g., an implantable pendant microphone device).

Implantable auxiliary devices augment a primary device, such as by placing components in a beneficial location remote from the implantable primary device. For instance, an implantable primary device may be implanted at a location behind a recipient's ear. While that location may advantageous for the stimulator assembly, it may be beneficial to locate a microphone away from the stimulator device, such as at a location that is less likely to be covered by headwear (e.g., a hat) or in a location more beneficial for receiving desired signals. Auxiliary devices can also be used to expand the capabilities of the implantable primary device without needing to replace the entire implantable device. The auxiliary device is connected to the primary device by an implantable cable. The cable can be of various lengths, such as about 5 cm, about 20 cm, or a different length.

Traditionally auxiliary devices are powered by the implantable primary device and lack their own battery. As a result, simultaneously, a data signal flows from the auxiliary device to the implantable primary device and a power signal flows from the implantable primary device to the auxiliary device. To support the simultaneous flow of power and data signals, the cable connecting the implantable primary device and the auxiliary device includes four wires electrically connecting the devices. As the number of wires increases, so too does the thickness of the cable, as well as the number of feedthroughs of the devices. Such increased bulk can be undesirable in implantable devices.

In some instances, the implantable primary device and the implantable auxiliary device are connected via a two-wire interface. The reduction to two wires is facilitated by interleaving power and data within the wires. This process includes transferring the data signal in a non-continuous way as digitized packets (e.g., via data packetizing). Advantageously, such digital data transfer improves the audio quality and resistance to interference. However such transfer method and the required hardware integration can be complex, with quasi-simultaneous power and data transfer in an opposite directions often being required. Moreover the wire interface often needs to be free of direct current and insulated from the tissue stimulation currents.

Examples disclosed herein can provide technical improvements over traditional techniques for interfacing between an implantable primary device and an implantable auxiliary device.

An example includes a system having a stimulator device and an auxiliary device connected by a cable. The auxiliary device has a small rechargeable battery. The system operates in different modes and uses a simplified protocol over a simplified cable (e.g., having a two-wire interface) to provide functionality. The system can be configured to, based on the system being in a first mode or a second mode, control charging of the auxiliary device battery from the stimulator device over the cable and control transmission of an auxiliary device signal from the auxiliary device to the implantable stimulator device over the cable. The system is configured to operate in the first mode while an external processor device is present and operate in the second mode while the external processor device is absent. Alternatively, the system is configured to operate in the first mode while the implantable stimulator device is coupled with an external processor device and operate in the second mode while the implantable stimulator device is not coupled with the external processor device.

Continuing the example, in the first mode (e.g., an external operation mode in which an external processor device is coupled to the stimulator device), the auxiliary device battery is connected to the cable and is recharged from the stimulator device. In the first mode, there is no data transfer from the auxiliary device (e.g., an audio signal from a microphone of the auxiliary device) to the stimulator device, and only power is transferred from the stimulator device to the auxiliary device over the wires of the cable. In the first mode, the stimulator device may receive power over the transcutaneous link to charge its own battery.

Continuing the example, in the second mode (e.g., an invisible operation mode lacking an external device coupled to the stimulator device), an auxiliary device transmits an auxiliary device signal over the wires of the cable and there is no power transmitted over the wires of the cable to charge the auxiliary device battery. Going from first mode to the second mode, the energy flow to recharge the auxiliary device battery is stopped. Instead, the auxiliary device signal emanating from the auxiliary device flows to the stimulator device over the wires of the cable. While operating in the second mode, the auxiliary device battery powers all active components inside the auxiliary device. For instance, the auxiliary device may include such active components as a radio transceiver (e.g., a short range radio device or a magnetic induction radio), one or more active microphone elements, and one or more low-noise operational amplifiers, among others.

Advantageously, such an arrangement requires fewer wires in the cable between the auxiliary device and the stimulator device (e.g., using only two wires rather than three or more). Further, the interface is simplified which is easier to manufacture and maintain. For instance, fewer feedthroughs are needed to connect the stimulator and auxiliary devices. And the data communication from the auxiliary device to the stimulator device can be made using a simple protocol. For instance, where the auxiliary device signal includes audio, the audio can be transferred as an analog or digital (e.g., raw, modulated, radiofrequency, pulse width modulation, S/D, or phase encoding, among others) signal rather than using TDMA or interleaving power and data. Further, improved power efficiency is achieved while the system operates in the second mode because the auxiliary device includes its own power source. The auxiliary device battery is small and able to be recharged quickly.

Cochlear Implant System

FIG. 1 depicts an example cochlear implant system that can benefit from the technologies disclosed herein. In particular, FIG. 1 illustrates an example cochlear implant system 110 that includes an implantable component 144 typically having an internal receiver/transceiver unit 132, a stimulator unit 120, and an elongate lead 118. The internal receiver/transceiver unit 132 permits the cochlear implant system 110 to receive and/or transmit signals to an external device 150. The external device 150 can be a button sound processor worn on the head that includes an external coil 130 (e.g., a receiver/transceiver coil) and sound processing components. Alternatively, the external device 150 can be a transmitter/transceiver coil in communication with a behind-the-ear device that includes the sound processing components and microphone.

The implantable component 144 includes an internal coil 136, and preferably, a magnet (not shown) fixed relative to the internal coil 136. The magnet can be embedded in a pliable silicone or other biocompatible encapsulant, along with the internal coil 136. Signals sent generally correspond to external sound 113. The internal receiver/transceiver unit 132 and the stimulator unit 120 are hermetically sealed within a biocompatible housing, sometimes collectively referred to as a stimulator/receiver unit. Included magnets (not shown) can facilitate the operational alignment of the external and internal coils, enabling the internal coil 136 to receive power and stimulation data from the external coil 130. The external coil 130 is contained within an external portion. The elongate lead 118 has a proximal end connected to the stimulator unit 120, and a distal end 146 implanted in a cochlea 140 of the recipient. The elongate lead 118 extends from stimulator unit 120 to the cochlea 140 through a mastoid bone 119 of the recipient.

In certain examples, the external coil 130 transmits electrical signals (e.g., power and stimulation data) to the internal coil 136 via a radio frequency (RF) link. The internal coil 136 is typically a wire antenna coil having of multiple turns of electrically insulated single-strand or multi-strand platinum or gold wire. The electrical insulation of the internal coil 136 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Figure 2:
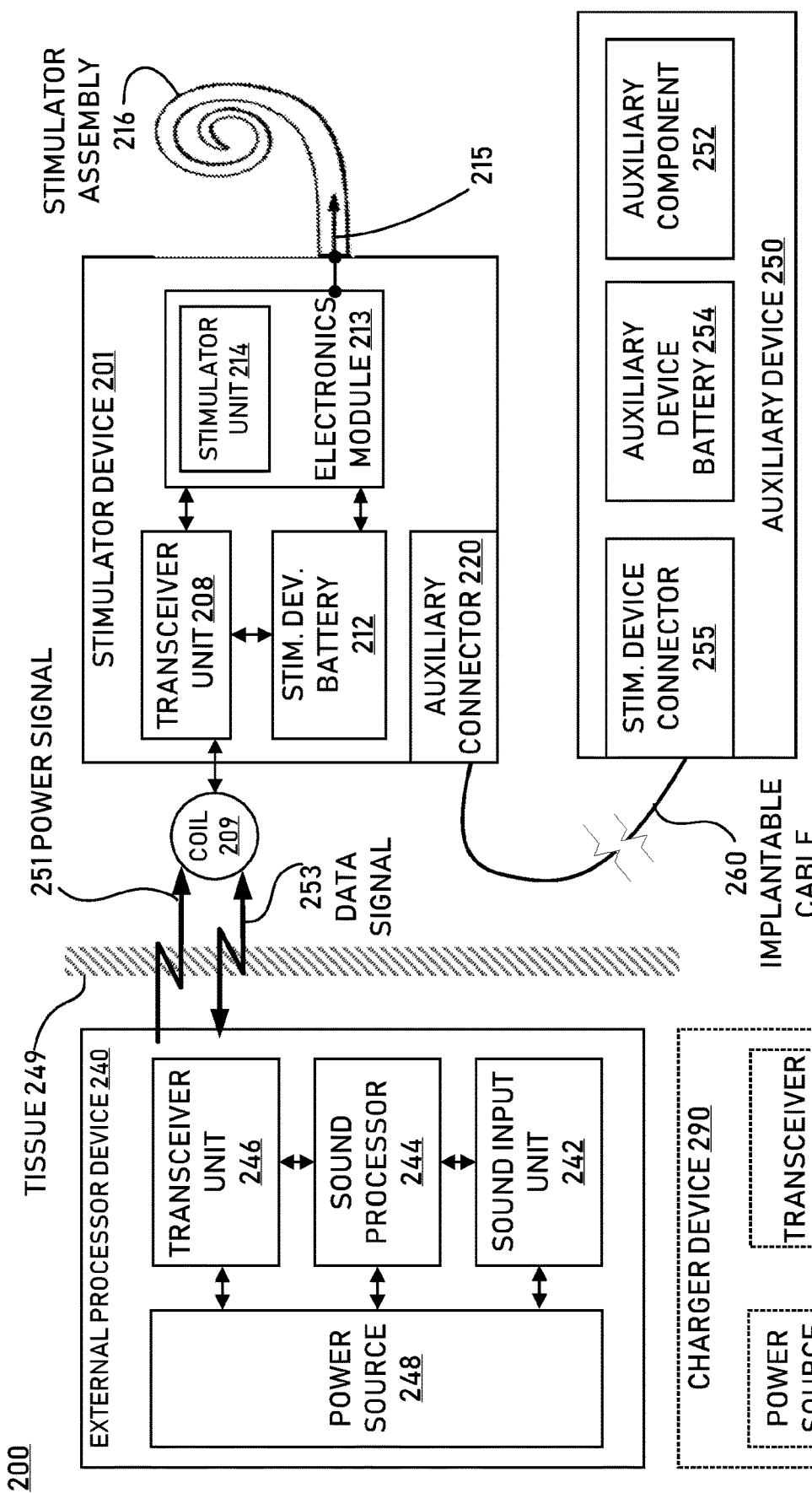
FIG. 2 is a functional block diagram of an auditory prosthesis system that can benefit from techniques described herein.

The implantable component 144 further includes an auxiliary device (not shown), such as the auxiliary device described in relation to FIG. 2.

FIG. 2 is a functional block diagram of an auditory prosthesis system 200 that can benefit from techniques described herein. The auditory prosthesis system 200 includes a stimulator device 201 and an external processor device 240. In some examples, the stimulator device 201 corresponds to the implantable component 144 of FIG. 1. In examples, the stimulator device 201 is an implantable stimulator device configured to be implanted beneath a recipient's tissue 249 (e.g., skin). In examples, the stimulator device 201 includes a biocompatible housing. The external processor device 240 is a device configured to couple with (e.g., wirelessly) the stimulator device 201 to provide additional functionality. In examples, the external processor device 240 corresponds to the external device 150 of FIG. 1. In examples, the auditory prosthesis system 200 includes a charger device 290 in addition to or instead of the external processor device 240.

In the illustrated example, the stimulator device 201 includes a transceiver unit 208, a coil 209, a stimulator device battery 212, an electronics module 213, a stimulator assembly 216, and an auxiliary connector unit 220. The stimulator device 201 further includes a hermetically sealed, biocompatible housing enclosing one or more of the components.

The transceiver unit 208 is configured to transcutaneously receive a power signal 251 and/or a data signal 253 from the external processor device 240. As used herein, the transceiver unit 208 is a collection of one or more implanted components that form part of a transcutaneous energy or data transfer system. Further, transceiver unit 208 includes any number of components that receive or transmit a power signal 251 or data signal 253, such as the coil 209 for a magnetic inductive arrangement, an antenna for an alternative RF system, capacitive plates, or any other suitable arrangement. Various types of energy transfer, such as electromagnetic, capacitive and inductive transfer, can be used to usably receive the power signal 251 and/or the data signal 253 from the external processor device 240 at the stimulator device 201.

Stimulator device battery 212 is a component configured to store power. The stimulator device battery 212 includes, for example, one or more rechargeable batteries. As described below, power can be received from an external device, such as the external processor device 240, and stored in the stimulator device battery 212. The power can then be distributed to the other components of the stimulator device 201 as needed for operation.

The electronics module 213 can include one or more other components to provide auditory prosthesis functionality. In many examples, the electronics module 213 includes one or more components for receiving a signal and converting the signal into the stimulation signal 215. As illustrated the electronics module further includes a stimulator unit 214 (e.g., which may correspond to stimulator unit 120 of FIG. 1). The electronics module 213 can generate or control delivery of the stimulation signals 215 to the stimulator assembly 216.

In examples, the electronics module 213 includes one or more processors (e.g., central processing units) coupled to memory components (e.g., flash memory) storing instructions that when executed cause performance of an operation described herein. In examples, the electronics module generates and monitors parameters associated with generating and delivering the stimulus (e.g., output voltage, output current, or line impedance). In examples, the electronics module 213 generates a telemetry signal (e.g., a data signal 253) that includes telemetry data based on one or more of the parameters. The electronics module 213 can send the telemetry signal to the external processor device 240 or store the telemetry signal in memory for later use or retrieval.

The auxiliary connector unit 220 is a component of the stimulator device 201 for connecting the stimulator device 201 to the auxiliary device 250 via the implantable cable 260. In some examples the auxiliary connector unit 220 includes a port to which the implantable cable 260 is coupled, thereby electrically coupling the stimulator device 201 and the auxiliary device 250. In some examples, the auxiliary connector unit 220 includes one or more switches or other components for managing the flow of data or power across the implantable cable 260. In an example, the auxiliary connector unit 220 includes a switch for selectively permitting or preventing the flow of power from the stimulator device 201 to the auxiliary device 250 or the flow of data from the auxiliary device 250 to the stimulator device 201. For instance, the switch may be a MOSFET switch or a bipolar switch. To receive an auxiliary signal from the auxiliary device 250 at the stimulator device, the switch can be opened to conduct the output of the wires of the implantable cable to the electronics module 213.

The implantable cable 260 is a component comprising one or more wires for providing a wired electrical connection between the stimulator device 201 and the auxiliary device 250. In examples, the implantable cable 260 includes two wires, and the two wires are the only wires of the implantable cable 260 electrically connecting the stimulator device 201 and the auxiliary device 250. In examples, the wires are configured to transfer power or data based on a mode of system 200. In examples, the implantable cable 260 includes insulation. In examples, the insulation is biocompatible. In examples, the implantable cable 260 includes shielding to mitigate, for example, the susceptibility of the implantable cable 260 to outside influences, alternating current leakage, direct current leakage, or electromagnetic interference.

In the illustrated example, the stimulator assembly 216 is an electrode assembly that includes an array of electrode contacts disposed on a lead (e.g., as in the elongate lead 118 of FIG. 1). The lead may be inserted into the recipient's cochlea. The stimulator assembly 216 is configured to deliver stimulation signals 215 (e.g., electrical stimulation signals) generated by the stimulator unit 214 to the cochlea to cause a hearing percept in the recipient. In other examples, the stimulator assembly 216 is a vibratory actuator disposed inside or outside of a housing of the stimulator device 201 and configured to generate vibrations. The vibratory actuator receives the stimulation signals 215 and, based thereon, generates a mechanical output force in the form of vibrations. The actuator can deliver the vibrations to the skull of the recipient in a manner that produces motion or vibration of the recipient's skull, thereby causing a hearing percept by activating the hair cells in the recipient's cochlea via cochlea fluid motion.

In the illustrated example, the external processor device 240 includes a sound input unit 242, a sound processor 244, a transceiver unit 246, and a power source 248. The sound input unit 242 is a unit configured to receive sound input. The sound input unit 242 can be configured as a microphone, an electrical input for an FM hearing system, and/or another component for receiving sound input. The sound processor 244 is a processor configured to convert sound signals received from sound input unit 242 into external device data signals 253. The transceiver unit 246 is configured to send an external device power signal, an external device data signal 253, combinations thereof (e.g., by interleaving the signals), or other signals. The transceiver unit 246 can also be configured to receive power or data. The data signals from the sound processor 244 can be transmitted, using the transceiver unit 246, to the stimulator device 201 for use in providing stimulation.

The auxiliary device 250 is an implantable component remote from the stimulator device 201 and configured to provide an auxiliary signal to the stimulator device 201. In this manner, the auxiliary device 250 supports the stimulator device 201. The auxiliary device 250 includes a stimulator device connector unit 255, an auxiliary component 252 for generating the auxiliary signal, and an auxiliary device battery 254 for powering one or more components of the auxiliary device 250, such as the auxiliary component 252.

The stimulator device connector unit 255 is a component of the auxiliary device 250 enabling the connection to the auxiliary device 250 to the stimulator device 201 via the implantable cable 260. In some examples the stimulator device connector unit 255 includes a port to which the implantable cable 260 is coupled, thereby electrically coupling the stimulator device 201 and the auxiliary device 250. In some examples, the auxiliary connector unit 220 includes one or more signal conditioning components. In an example, the stimulator device connector unit 255 includes a rectifier for rectifying a power signal received over the implantable cable 260. For example, the stimulator device 201 is configured to provide power to charge the auxiliary device battery using an Alternating Current (AC) power signal rather than a Direct Current (DC) power signal. In implantable configurations, AC signals can be advantageous compared to DC signals to eliminate the risk of DC signals flowing through nearby tissue. The rectifier can be used to convert the AC signal transmitted over the implantable cable to a DC signal used by one or more components of the auxiliary device 250. In examples, the rectifier is a four-diode bridge electrically connected to the wires of the implantable cable 260. The configuration of the rectifier may inhibit the flow of the auxiliary signal from the auxiliary device 250 to the stimulator device 201 while a power signal is flowing from the stimulator device 201 to the auxiliary device 250. In examples, where the auxiliary component 252 produces an auxiliary signal (e.g., a microphone output audio signal), the auxiliary signal is likely weak (10-30 millivolts) such that the signal will not act on the diode bridge, which begins to conduct at a higher voltage (e.g., on the order of hundreds of millivolts). If there is no power being provided over the implantable cable 260 from the stimulator device 201, then the auxiliary signal does not pass through the bridge and flows unhindered to the stimulator device 201. In other examples, in addition to or instead of the use of a rectifier, the stimulator device connector unit 255 can include other components for controlling the flow of data or power over the implantable cable 260, such as one or more switches or other components.

The auxiliary component 252 is a component of the auxiliary device 250 that provides functionality to the system 200. For instance, the auxiliary component 252 generates an auxiliary signal provided from the auxiliary device 250 to the stimulator device 201. In an example, the auxiliary component 252 is one or more components of the group of: a microphone, a transcutaneous wireless audio link, a subcutaneous wireless audio link, a transcutaneous wireless stimulation data link, a subcutaneous wireless stimulation data link, and a telecoil, among other components. In an example, the auxiliary component 252 includes a microphone. The sounds detected by the microphone are provided to the stimulator device 201 (e.g., the electronics module thereof) as an auxiliary signal for use in generating the stimulation signals 215. In another example, the auxiliary component 252 includes an accelerometer that generates accelerometer signals that are provided to the stimulator device 201 as the auxiliary signal for use in generating the stimulation signals 215.

In an example, the auxiliary component 252 is a command receiver (e.g., for receiving commands sent of an RF protocol) to receive commands transmitted from another device (e.g., a non-implanted remote control device). In examples, the auxiliary component 252 is a sensor (e.g., magnetic field sensor) for detecting whether the system 200 is being subject to MRI (Magnetic Resonance Imaging) and for sending an auxiliary signal to deactivate or activate one or more components of the system 200 (e.g., the implantable stimulator 201) based thereon. In an example, the auxiliary component 252 controls the system 200 such that the implantable stimulator 201 is inoperable absent cooperation with the auxiliary component 252. In such examples, the auxiliary component 252 can act like a main control or key that permits operation of the implantable stimulator. In an example, the system 200 is configured such that the auxiliary battery 254 does not empty before the stimulator device battery 212.

The auxiliary device battery 254 is a rechargeable battery. In an example, the auxiliary device battery 254 is a lithium ion battery. In examples, the auxiliary device battery has a capacity of approximately 100 microampere hours.

The charger device 290 is an optional device configured to charge the stimulator device 201 by providing a power signal 251. The charger device 290 includes a power source 248 and a transceiver unit 246. Compared to the external processor device 240, the charger device 290 lacks a sound processor 244 and a sound input unit 242. As such, in many examples the charger device 290 provides only a power signal 251 and not a data signal 253. In some examples, the external processor device 240 can be set to a charger mode such that the external processor device 240 acts as a charger device (e.g., by disabling functionality to provide only a power signal 251 and not a data signal 253).

As should be appreciated, while a particular auditory prosthesis that can benefit from utilizing the disclosed techniques has been illustrated and discussed above, the disclosed monolithic medical device components can be integrated in any of a variety of implantable medical devices in accordance with many embodiments of the invention. The above discussion is not meant to suggest that the disclosed techniques are only suitable for implementation within systems akin to that illustrated in and described with respect to FIGS. 1 and 2. In general, additional configurations can be used to practice the methods and systems herein and/or some aspects described can be excluded without departing from the methods and systems disclosed herein.

Power and Data Signal Control System Using First and Second Modes

Figure 3A:
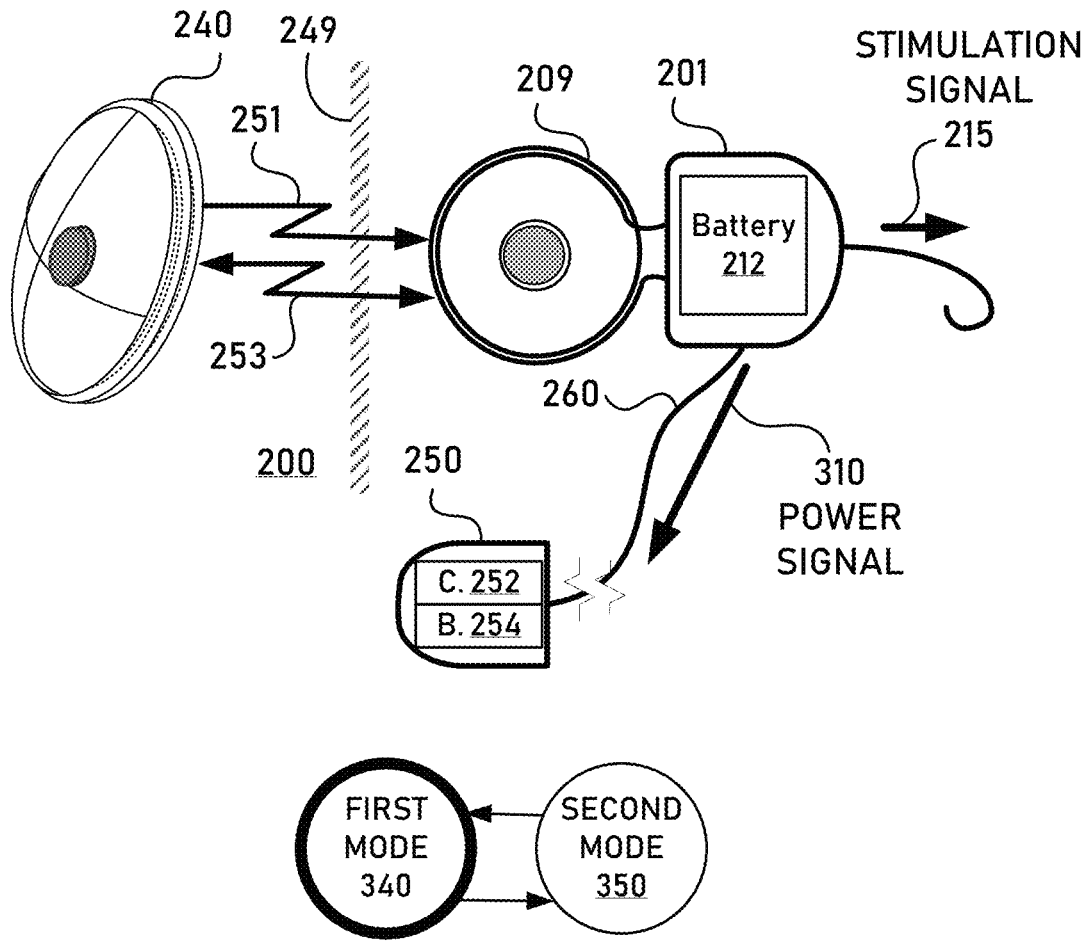
FIG. 3, which is made up of FIGS. 3A, 3B, and 3C, illustrates an auditory prosthesis system selectively operating in a first mode and a second mode in accordance with certain embodiments.
Figure 3B:
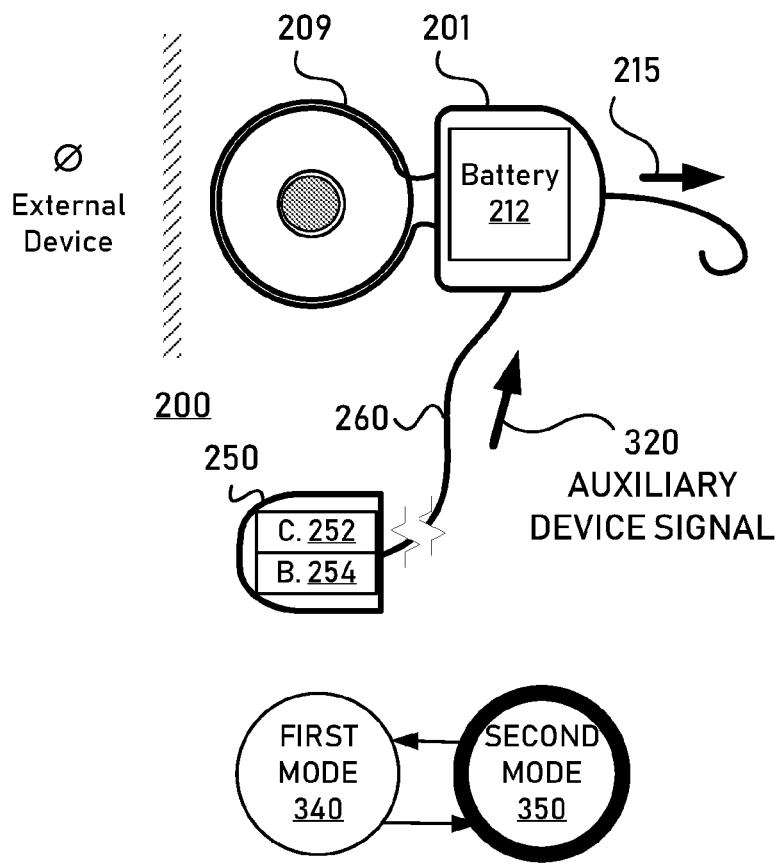
Figure 3C:
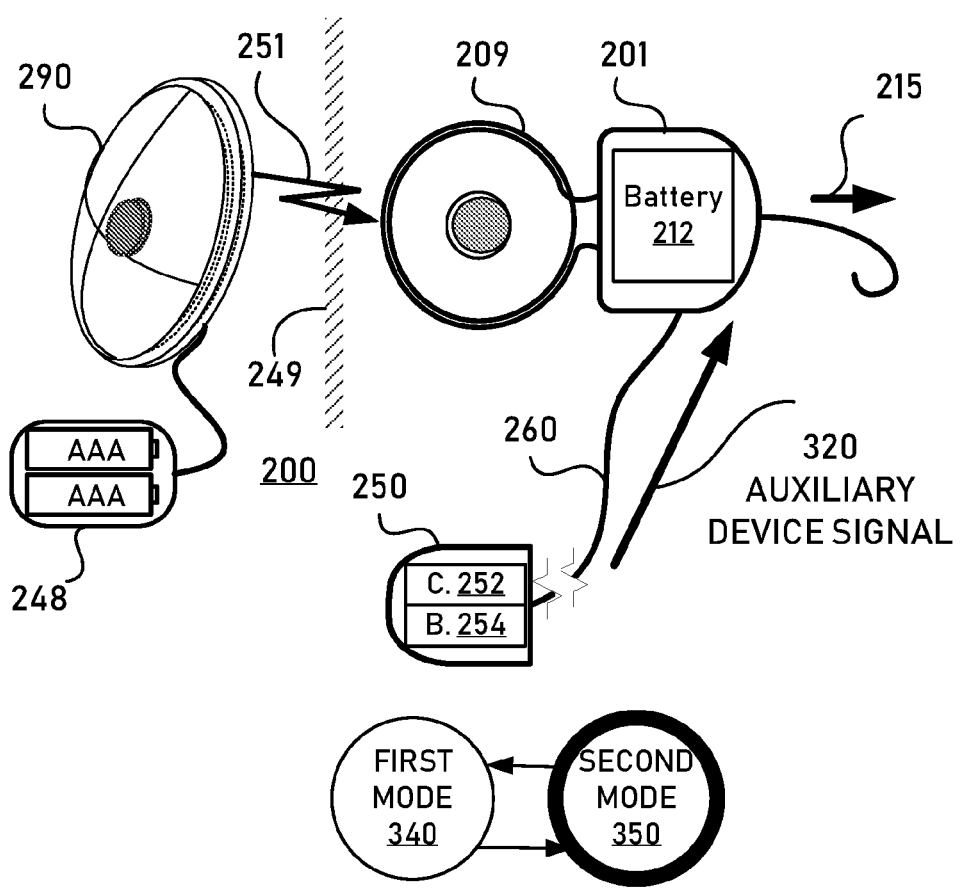

FIG. 3, which is made up of FIGS. 3A, 3B, and 3C, illustrates the auditory prosthesis system 200 selectively operating in a first mode 340 and a second mode 350 in accordance with certain embodiments. While the system 200 is illustrated in a particular configuration, embodiments of the invention can be implemented in other configurations and as part of other systems. The auditory prosthesis system 200 operates in the first mode 340 while the stimulator device 201 is coupled with the external processor device 240. The auditory prosthesis system 200 operates in the second mode 350 while the stimulator device 201 is not coupled with the external processor device 240. In examples, the auditory prosthesis system 200 automatically switches from the first mode 340 to the second mode 350 responsive to the stimulator device 201 lacking a connection with an external device. In examples, the auditory prosthesis system 200 automatically switches from the second mode 350 to the first mode 340 responsive to the stimulator device 201 having a connection with an external device.

As illustrated in FIG. 3A, the stimulator device 201 is coupled to the external processor device 240, and the auditory prosthesis system 200 is operating in the first mode 340. The coupling includes the external processor device 240 providing an external device power signal 251 and an external device data signal 253 to the coil 209 of the implanted stimulator device. While operating in the first mode 340, the stimulator device 201 provides power to charge the auxiliary device battery 254 via a stimulation device power signal 310 over the implantable cable 260. While operating in the first mode 340, the auxiliary device 250 receives the stimulation device power signal 310 and uses the stimulation device power signal 310 to charge the auxiliary device battery 254. While operating in the first mode 340, the stimulator device 201 does not receive data (e.g., as provided in an auxiliary device signal) from the auxiliary device 250 over the implantable cable 260. While operating in the first mode 340, the stimulator device 201 generates a stimulation signal 215 based on the external device data signal 253 received from the external processor device 240.

As illustrated in FIG. 3B, the stimulator device 201 is not coupled to an external device, and the auditory prosthesis system 200 is operating in the second mode 350. As illustrated, an external device is absent and the stimulator device 201 does not receive an external device power signal 251 or an external device data signal 253 from an external (e.g., non-implanted) source. While operating in the second mode 350, the stimulator device 201 receives the auxiliary device signal 320 from the auxiliary device 250 over the implantable cable. While operating in the second mode 350, the stimulator device 201 does not provide a stimulation device power signal 310 over the implantable cable 260 to charge the auxiliary device battery 254. While operating in the second mode 350, the auxiliary device 250 is self-powered from the auxiliary device battery 254. While operating in the second mode 350, the stimulator device 201 generates a stimulation signal 215 based on the auxiliary device signal 320 received from the auxiliary device 250.

As illustrated in FIG. 3C, the stimulator device 201 is coupled to a charger device 290, and the auditory prosthesis system 200 is operating in the second mode 350. As illustrated, the charger device 290 provides an external device power signal 251 and does not provide an external device data signal 253. As such, the implanted stimulator device 201 receives power from an external (e.g., non-implanted) source but not data. The stimulator device 201 charges the stimulator device battery 212 from the charger device 290. In the illustrated configuration, because the stimulator device 201 does not receive a data signal from an external device, the stimulator device 201 operates in the second mode 350 to receive the auxiliary device signal 320 from the auxiliary device 250 over the implantable cable 260. While operating in the second mode 350, the stimulator device 201 does not provide a stimulation device power signal 310 over the implantable cable 260 to charge the auxiliary device battery 254. While operating in the second mode 350, the auxiliary device 250 is self-powered from the auxiliary device battery 254. While operating in the second mode 350, the stimulator device 201 generates a stimulation signal 215 based on the external device data signal 253 received from the auxiliary device 250.

Power and Data Signal Control Process Using First and Second Modes

Figure 4:
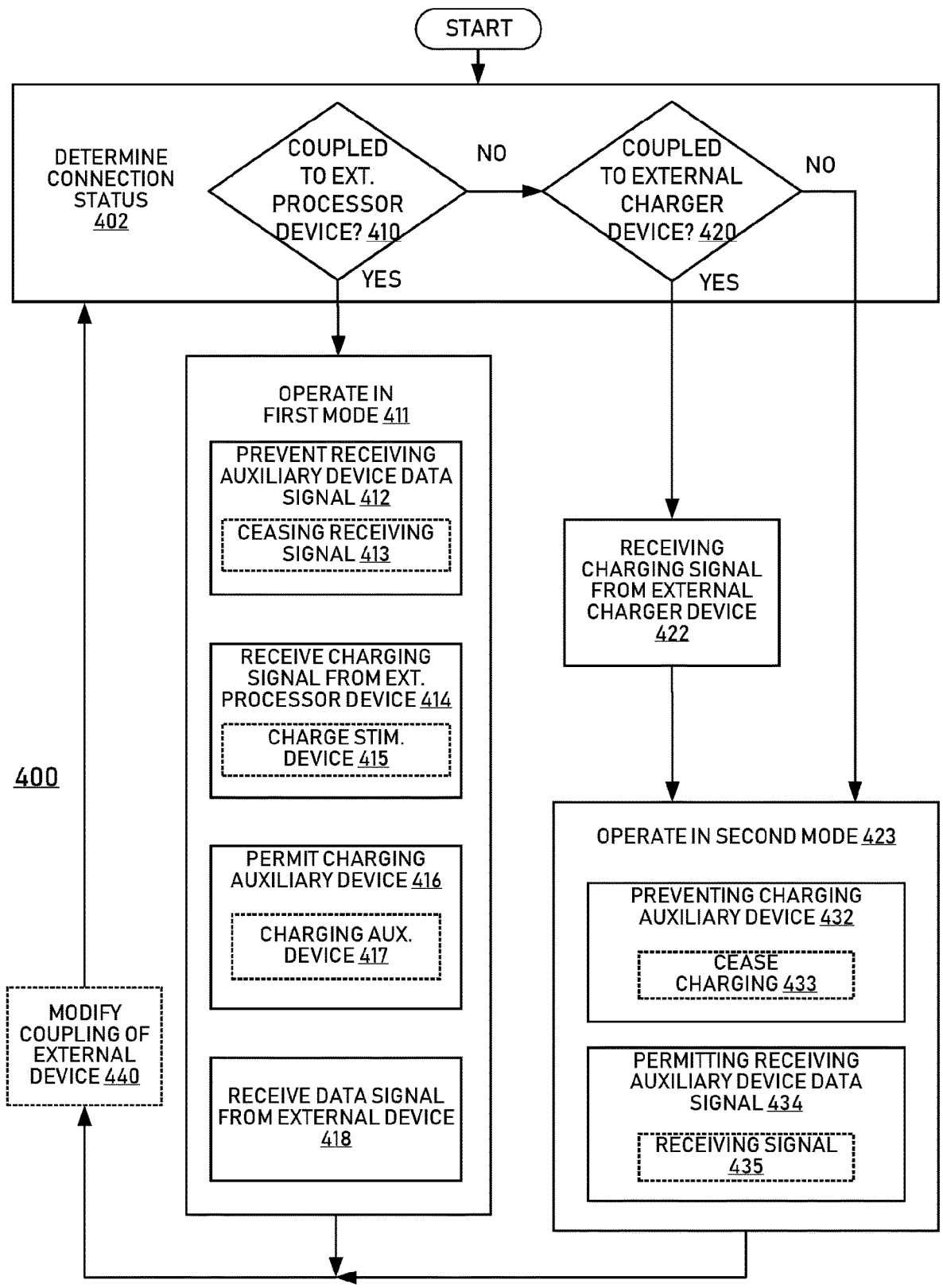
FIG. 4 illustrates a process for controlling power and data signals of an auditory prosthesis system in accordance with certain embodiments.

FIG. 4 illustrates a process 400 for controlling power and data signals of the auditory prosthesis system 200 in accordance with certain embodiments. While one example process 400 is illustrated, disclosed embodiments can be implemented as part of a variety of other processes. The illustrated process 400 begins with operation 402.

Operation 402 includes determining a connection status of the stimulator device 201. Determining the connection status includes determining whether the stimulator device 201 is coupled with an external device (e.g., a non-implanted device), such as the external processor device 240 or the charger device 290. The stimulator device 201 being coupled with an external device can include various kinds of couplings, such as an inductive coupling, a magnetic coupling, resonant coupling, and radiofrequency coupling, among other kinds of coupling.

Determining the connection status can be performed using various techniques. In examples, the determining can include determining whether the stimulator device 201 has an external device data connection. In examples, the stimulator device 201 can have an external device data connection when it is coupled to an external device and is capable of receiving an external device data signal 253 from the external device. For instance, the external device is configured to provide an external device data signal 253 to the stimulator device 201 and the stimulator device 201 is configured to receive the data signal for the external device.

For instance, determining whether the stimulator device 201 has an external device data connection can include determining whether the stimulator device 201 recently received an external device data signal 253 from an external device (e.g., over the coil 209). As noted above, the external processor device 240 may periodically transmit an external device data signal 253 to the stimulator device 201. As a result, the stimulator device 201 (e.g., the electronics module thereof 213) can determine whether the stimulator device 201 is coupled with an external device based on a time since an external device data signal 253 was last received. If the stimulator device 201 receives an external device data signal 253 within a threshold period of time (e.g., 200 milliseconds or 1 second), the stimulator device 201 may then determine that the stimulator device 201 is coupled with an external device. But if an external device data signal 253 was not received within the threshold period of time, the stimulator device 201 may then determine that the stimulator device 201 is not coupled with an external device. In other examples, the stimulator device 201 can emit a ping via the transceiver unit 208 and determine whether a response is received from an external device. If a response is received, then the stimulator device may determine that there is a coupling with an external device.

Similarly, determining the connection status can include determining whether the stimulator device 201 recently received an external device power signal from an external device (e.g., over the coil 209). As noted above, the external processor device 240 or the charger device 290 may periodically transmit an external device power signal 251 to the stimulator device 201 to charge the stimulator device battery 212. As a result, the stimulator device 201 (e.g., the electronics module thereof 213) can determine whether the stimulator device 201 is coupled with an external device based on a time since an external device power signal 251 was last received from an external device. If the stimulator device 201 receives an external device power signal 251 within a given period of time, the stimulator device 201 may then determine that the stimulator device 201 is coupled with an external device. But if an external device power signal 251 was not received within the period of time, the stimulator device 201 may then determine that the stimulator device 201 is not coupled with an external device.

In example, the determining can include the stimulator device 201 using a sensor or an RF diode detector coupled to the electronics module 213. In example, the sensor or diode detector is configured to detect the presence or absence of an external device. In an example, the sensor or RF diode detector is configured to detect a magnetic field. In an example the sensor is a Reed switch or a Hall-effect sensor. And the output of the sensor or RF diode detector can be used to determine the presence or an absence of an external device. For instance, the sensor or RF diode detector provides an output when the stimulator device 201 is coupled to an external device. The determination may be made based on the output of the sensor or the RF diode detector.

In examples, the determining can include the stimulator device 201 determining whether the stimulator device 201 has a connection with the auxiliary device 250 and, if so, continuing the method 400. Otherwise, the stimulator device 201 can exit the method and return and error (e.g., send an error code as part of a telemetry signal to the external processor device 240).

In examples, the operation 402 includes operation 410 and operation 420.

Operation 410 includes determining whether the stimulator device 201 is coupled to an external processor device 240. Determining whether the implanted stimulator device is coupled to the external processor device 240 can be based on the determined connection status. In examples, the presence of the external processor device 240 is characterized by the presence or absence of an external device data signal 253 being recently received at the stimulator device 201 from the external processor device 240. Responsive to the stimulator device 201 being coupled to the external processor device 240, the flow of the process 400 moves to operation 411. Responsive to the stimulator device 201 lacking a coupling with the external processor device 240, the flow of the process 400 moves to operation 420.

Operation 411 includes the auditory prosthesis system 200 operating in the first mode 340. In examples, operating in the first mode 340 is characterized by the stimulator device 201 charging the auxiliary device 250 and the stimulator device 201 using an external device data signal 253 from the external processor device 240 rather than a data signal from the auxiliary device 250 (e.g., as provided by the auxiliary device signal 320). Operation 411 can include various operations including operation 412, operation 414, operation 416, and operation 418.

Operation 412 includes preventing receiving, at the stimulator device 201, an auxiliary device signal 320. In examples, this operation includes activating a switch or other software or hardware component of one or both of the stimulator device 201 and the auxiliary device 250, such that the auxiliary device signal 320 is prevented from being usefully received at the stimulator device 201. This can include, for example, preventing the auxiliary device signal 320 from leaving the auxiliary device 250 (e.g., preventing the auxiliary device 250 from transmitting the auxiliary device signal 320 over the implantable cable 260), preventing the auxiliary device signal 320 from being usably received at the stimulator device 201, preventing the electronics module 213 from using the auxiliary device signal 320, ignoring the auxiliary device signal 320 at the stimulator device 201, and not listening for the auxiliary device signal 320 at the stimulator device 201, among other actions.

In examples, operation 412 includes operation 413, which includes ceasing receiving the auxiliary device signal 320. In examples, the stimulator device 201 may receive the auxiliary device signal 320 for a time and then no longer receive the auxiliary device signal 320 (e.g., based on at least one of the actions described in operation 412).

Operation 414 includes receiving a charging signal (e.g., the power signal 251) from the external processor device 240. In examples, operation 414 includes operation 415. This operation 414 includes the stimulator device 201 receiving the external device power signal 251 from the external processor device 240. The external device power signal 251 may be, for example, a resonant, electromagnetic, capacitive, or inductive power transfer signal. In examples, operation 414 further includes operation 415. Operation 415 includes charging the stimulator device battery 212 using the external device power signal 251.

Operation 416 includes permitting charging the auxiliary device 250. In examples, this operation includes activating a switch or other software or hardware component of one or both of the stimulator device 201 and the auxiliary device 250, such that the stimulator device 201 is permitted to charge the auxiliary device 250. This can include, for example, permitting a stimulation device power signal 310 to travel from the stimulator device 201 via the implantable cable 260 to the auxiliary device 250, permitting the auxiliary device 250 to receive the stimulation device power signal 310, permitting the auxiliary device 250 to charge the auxiliary device battery 254 using the stimulation device power signal 310, among other actions. In examples, operation 416 includes operation 417. Operation 417 includes charging the auxiliary device battery 254 using the stimulation device power signal 310. In examples, charging the auxiliary device battery 254 includes charging over the implanted cable 260, such as supplying power using two wires of the implanted cable 260. In examples, the two wires are the same two wires used to transmit the auxiliary device signal 320.

Operation 418 includes receiving an external device data signal 253 from the external processor device 240. In examples, the stimulator device 201 receives the external device data signal 253 from the external processor device 240. For instance, the external processor device 240 receives a sound signal at the sound input unit 242, converts sound signals received from sound input unit 242 into external device data signals 253 using the sound processor 244, and then transmits the external device data signal 253 to the stimulator device 201 using the transceiver unit 246. The stimulator device 201 can then receive the external device data signal 253 at the transceiver unit 208 via the coil 209. The stimulator device 201 can generate a stimulation signal 215 based on the external device data signal 253 using the electronics module 213 (e.g., using the stimulator unit 214 thereof). In some examples, during or following operation 411 the flow moves to operation 440 where the coupling is modified. In other examples, the flow moves to operation 402.

Operation 440 includes modifying the coupling of an external device. This operation 440 can include, for example, coupling an external device to the stimulator device 201, decoupling an external device from the stimulator device 201, deactivating the external device, activating the external device, combinations thereof, or another action. In examples, the operation 440 includes coupling (e.g., magnetically or electrically) the external processor device 240 to the implanted stimulator device 201 by forming one or both of an external device power signal 251 and a data signal 253 connection from the external processor device 240 to the implanted stimulator device 201. The external device can be, for example, the external processor device 240, the charger device 290, or another device. Following operation 440, the flow can return to operation 402.

Operation 420 includes determining whether the implanted stimulator device is coupled to a charger device 290. Determining whether the implanted stimulator device is coupled to the charger device 290 can be based on the determined connection status. In examples, the presence of the charger device is characterized by the presence or absence of an external device power signal 251 being recently received at the stimulator device 201 and usable for charging stimulator device battery 212. In an example, the presence of the charger device 290 is determined if the stimulator device 201 receives a power signal 251 but no data signal 253 from an external device. Responsive to the stimulator device 201 being coupled to a charger device 290, the flow moves to operation 422. Responsive to the stimulator device 201 lacking a coupling with a charger device 290, the flow of the process 400 moves to operation 423.

Operation 422 includes receiving a charging signal (e.g., in the form of a power signal 251) from the charger device 290. In examples, receiving the charging signal includes the stimulator device 201 receiving an external device power signal 251 from the charger device 290. The external device power signal 251 may be, for example, a resonant, electromagnetic, capacitive, or inductive power transfer signal. In examples, operation 422 further includes charging the stimulator device battery 212 using the external device power signal 251 from the charger device. Following operation 422, the flow moves to operation 423.

Operation 423 includes operating in the second mode 350. In examples, operating in the second mode 350 is characterized by the stimulator device 201 using an auxiliary device signal 320 from the auxiliary device 250 rather than a data signal from an external device. Operation 423 can include various operations including operation 432 and operation 434.

Operation 432 includes preventing charging the auxiliary device battery 254. In examples, this operation 432 includes activating a switch or other software or hardware component of one or both of the stimulator device 201 and the auxiliary device 250, such that the stimulator device 201 is prevented from charging the auxiliary device 250 or that the auxiliary device 250 is prevented from charging the auxiliary device battery 254. This can include, for example, preventing a stimulation device power signal 310 from traveling from the stimulator device 201 via the implantable cable 260 to the auxiliary device 250, preventing the auxiliary device 250 from receiving the stimulation device power signal 310, preventing the auxiliary device 250 from charging the auxiliary device battery 254 using the stimulation device power signal 310, among other actions. In examples, operation 432 includes operation 433. Operation 433 includes ceasing charging the auxiliary device battery 254 using the stimulation device power signal 310. In examples, the auxiliary device 250 may receive a stimulation device power signal 310 for a time and then no longer receive the stimulation device power signal 310 (e.g., based on at least one of the actions described in operation 432).

Operation 434 includes permitting receiving an auxiliary device signal 320. In examples, this operation includes activating a switch or other software or hardware component of one or both of the stimulator device 201 and the auxiliary device 250, such that the auxiliary device signal 320 is permitted to be usefully received at the stimulator device 201. This can include, for example, permitting the auxiliary device signal 320 to leave the auxiliary device 250 (e.g., enabling the auxiliary device 250 to transmit the auxiliary device signal 320 over the implantable cable 260), permitting the auxiliary device signal 320 to be usably received at the stimulator device 201, permitting the electronics module 213 to use the auxiliary device signal 320, obtaining the auxiliary device signal 320 at the stimulator device 201, listening for the auxiliary device signal 320 at the stimulator device 201, activating the auxiliary component 252, and generating the auxiliary device signal 320 using the auxiliary component 252, among other actions. In examples, operation 434 includes operation 435.

Operation 435 includes receiving the auxiliary device signal 320 at the stimulator device 201. For instance, the auxiliary device 250 receives a signal (e.g., a sound signal) at the auxiliary device 250, converts the signal into an auxiliary device signal 320, and then transmits the auxiliary device signal 320 over the implantable cable 260. In examples, receiving the auxiliary device signal 320 includes receiving the auxiliary device signal 320 over two wires of the implantable cable 260. In examples, the two wires are the same two wires over which the power signal 310 is supplied. The stimulator device 201 can generate a stimulation signal 215 based on the external device data signal 253 using the electronics module 213 (e.g., using the stimulator unit 214 thereof).

In some examples, during or following operation 423 the flow moves to operation 440 where the coupling is modified. In other examples, the flow returns to operation 402.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. For examples, while certain technologies described herein were primarily described in the context of auditory prostheses (e.g., cochlear implants), technologies disclosed herein are applicable to medical devices generally (e.g., medical devices providing pain management functionality or therapeutic electrical stimulation, such as deep brain stimulation). In general, additional configurations can be used to practice the methods and systems herein and/or some aspects described can be excluded without departing from the methods and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and methods to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

The invention claimed is:

1. A method comprising:
   while an implanted stimulator device is coupled with an external processor device:
      preventing receiving of an auxiliary device signal over an implanted cable connecting the implanted stimulator device with an implanted auxiliary device; and
      permitting charging of an auxiliary device battery of the implanted auxiliary device over the implanted cable; and
   while the implanted stimulator device is not coupled with the external processor device:
      preventing charging of the auxiliary device battery of the implanted auxiliary device over the implanted cable; and
      permitting receiving of the auxiliary device signal at the implanted stimulator device over the implanted cable.

2. The method of claim 1, further comprising:
   determining a connection status;
   responsive to the connection status indicating that the implanted stimulator device is coupled with the external processor device:
      charging the auxiliary device battery over the implanted cable; and
      ceasing receiving of the auxiliary device signal; and
   responsive to the connection status indicating that the implanted stimulator device is not coupled with the external processor device:
      ceasing charging of the auxiliary device battery over the implanted cable; and
      receiving the auxiliary device signal at the implanted stimulator device over the implanted cable.

3. The method of claim 2,
   wherein charging the auxiliary device battery over the implanted cable includes:
      supplying power using two wires of the implanted cable; and
   wherein receiving the auxiliary device signal at the implanted stimulator device over the implanted cable includes:
      receiving the auxiliary device signal over the two wires.

4. The method of claim 1, further comprising:
   coupling the external processor device to the implanted stimulator device by forming an external device power signal and data signal connection from the external processor device to the implanted stimulator device.

5. The method of claim 1, further comprising:
   while the implanted stimulator device is coupled with the external processor device:
      receiving an external processor device data signal from the external processor device at the implanted stimulator device; and
      charging a stimulator device battery of the implanted stimulator device using the external processor device.

6. The method of claim 1, further comprising:
   producing, via an auxiliary component of the implanted auxiliary device, the auxiliary device signal,
   wherein the auxiliary component is a data source selected from a group consisting of: a microphone, a transcutaneous wireless audio link, a subcutaneous wireless audio link, a transcutaneous wireless stimulation data link, a subcutaneous wireless stimulation data link, and a telecoil.

7. The method of claim 1, further comprising:
   while (a) the implanted stimulator device is not coupled with the external processor device and (b) the implanted stimulator device is coupled with a charger device:
      receiving the auxiliary device signal at the implanted stimulator device over the implanted cable; and
      charging a stimulator device battery of the implanted stimulator device using the charger device.

8. An implantable medical system comprising:
   an implantable stimulator device;
   an implantable auxiliary device having an auxiliary device battery and an auxiliary component; and
   an implantable cable configured to electrically connect the implantable stimulator device and the implantable auxiliary device,
   wherein the implantable medical system comprises at least one processor configured to, based on the implantable medical system being in a first mode or a second mode:
      control charging of the auxiliary device battery from the implantable stimulator device over the implantable cable by permitting the charging while in the first mode and preventing the charging while in the second mode; and
      control transmission of an auxiliary device signal from the auxiliary component to the implantable stimulator device over the implantable cable by preventing the transmission while in the first mode and permitting the transmission while in the second mode.

9. The implantable medical system of claim 8, wherein the implantable stimulator device comprises a switch for selectively permitting and preventing the charging of the auxiliary device battery from the implantable stimulator device based on the implantable medical system being in the first mode or the second mode.

10. The implantable medical system of claim 8, wherein the implantable medical system is configured to operate in the first mode while an external processor device is present and operate in the second mode while the external processor device is absent.

11. The implantable medical system of claim 8, wherein the implantable medical system is configured to operate in the first mode while the implantable stimulator device is coupled with an external processor device and operate in the second mode while the implantable stimulator device is not coupled with the external processor device.

12. The implantable medical system of claim 8, wherein the implantable cable comprises only two wires electrically connecting the implantable stimulator device and the implantable auxiliary device.

13. The implantable medical system of claim 8, wherein the implantable stimulator device comprises:
   a coil for wirelessly coupling with an external processor device;
   a stimulator device battery; and
   a stimulator assembly configured to deliver stimulation signals to a cochlea of a recipient.

14. The implantable medical system of claim 8, wherein the auxiliary component comprises a source selected from a group consisting of: a microphone, a transcutaneous wireless audio link, a subcutaneous wireless audio link, a transcutaneous wireless stimulation data link, a subcutaneous wireless stimulation data link and a telecoil.

15. The implantable medical system of claim 8, further comprising an external processor device configured to wirelessly provide an external device power signal and data signal to the implantable stimulator device.

16. An implantable medical apparatus comprising:
- at least one processor; and
- a wired interface between an implantable stimulator device and an implantable auxiliary device, wherein the at least one processor controls the wired interface to permit charging of the implantable auxiliary device from the implantable stimulator device, and to prevent the implantable stimulator device from receiving data from the implantable auxiliary device, while the implantable stimulator device operates in a first mode; and
- wherein the at least one processor controls the wired interface to prevent the implantable stimulator device from charging the implantable auxiliary device, and to permit receiving of data at the implantable stimulator device from the implantable auxiliary device, while the implantable stimulator device operates in a second mode.

17. The implantable medical apparatus of claim 16,
- wherein the implantable stimulator device is configured to operate in the first mode while having an external device data connection; and
- wherein the implantable stimulator device is configured to operate in the second mode while lacking the external device data connection.

18. The implantable medical apparatus of claim 16, wherein the wired interface comprises a cable having only two wires electrically connecting the implantable stimulator device and the implantable auxiliary device.

19. The implantable medical apparatus of claim 16, further including:
- a switch for selectively permitting the charging of the implantable auxiliary device from the implantable stimulator device based on the implantable stimulator device operating in the first mode, and preventing the charging of the implantable auxiliary device from the implantable stimulator device based on the implantable stimulator device operating in the second mode.

20. The implantable medical apparatus of claim 16,
- wherein the implantable stimulator device is configured to operate in the second mode (a) while lacking an external device data connection with an external processing device and (b) while having an external device power connection with a charger device; and
- wherein the wired interface permits charging of the implantable stimulator device using the charger device while the implantable stimulator device operates in the second mode.

* * * * *